US008940717B2

(12) United States Patent
Kiguchi et al.

(10) Patent No.: US 8,940,717 B2

(45) Date of Patent: Jan. 27, 2015

(54) PLANT DISEASE CONTROLLING COMPOSITION AND METHOD FOR CONTROLLING PLANT DISEASE

(75) Inventors: So Kiguchi, Toyonaka (JP); Soichi Tanaka, Nishinomiya (JP); Mayuko Ozawa, Toyonaka (JP); Atsushi Iwata, Takarazuka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

(21) Appl. No.: 13/580,901

(22) PCT Filed: Mar. 2, 2011

(86) PCT No.: PCT/JP2011/055438

§ 371 (c)(1),
(2), (4) Date: Aug. 23, 2012

(87) PCT Pub. No.: WO2011/108759

PCT Pub. Date: Sep. 9, 2011

(65) Prior Publication Data

US 2012/0322765 A1 Dec. 20, 2012

(30) Foreign Application Priority Data

Mar. 3, 2010 (JP) ................................ 2010-046377

(51) Int. Cl.
*A01N 37/38* (2006.01)

(52) U.S. Cl.
CPC ..................................... *A01N 37/38* (2013.01)
USPC ............. 514/81; 514/141; 514/146; 514/188; 514/223

(58) Field of Classification Search
CPC ....... A01N 37/38; A01N 35/04; A01N 37/34; A01N 37/52
USPC ........................................... 514/81, 141, 146
See application file for complete search history.

(56) References Cited

U.S. PATENT DOCUMENTS

| | | | |
|---|---|---|---|
| 5,948,819 A | 9/1999 | Ohtsuka et al. | |
| 6,313,150 B1 | 11/2001 | Ohtsuka et al. | |
| 6,444,692 B1 | 9/2002 | Schelberger et al. | |
| 2003/0176459 A1 | 9/2003 | Yamamoto et al. | |
| 2004/0204470 A1 | 10/2004 | Elbe et al. | |
| 2005/0065031 A1 * | 3/2005 | Forster | 504/133 |
| 2007/0173408 A1 | 7/2007 | Blasco et al. | |
| 2010/0016157 A1 | 1/2010 | Forster | |

FOREIGN PATENT DOCUMENTS

| | | | | |
|---|---|---|---|---|
| CA | 2199422 A1 | 3/1996 | | |
| CN | 1145061 A | 3/1997 | | |
| CN | 1930977 A | 3/2007 | | |
| CN | 101088336 A | 12/2007 | | |
| CN | 100364400 C | 1/2008 | | |
| CN | 101379979 A | 3/2009 | | |
| FR | 2 740 005 A1 | 4/1997 | | |
| WO | WO 95/27693 A1 | 10/1995 | | |
| WO | WO 96/07633 A1 | 3/1996 | | |
| WO | WO 01/92231 A1 | 12/2001 | | |
| WO | WO 02/10101 A1 | 2/2002 | | |
| WO | WO 03/010149 A1 | 2/2003 | | |
| WO | 03/045147 A1 | 6/2003 | | |
| WO | WO 03/074491 A1 | 9/2003 | | |
| WO | WO 2005-087773 A1 | 9/2005 | | |
| WO | WO 2009/119872 A2 * | 10/2009 | | A01N 43/88 |
| WO | WO 2009/119872 A2 | 10/2009 | | |

OTHER PUBLICATIONS

Delp, C.; Title: Coping with Resistance to Plant Disease; Plant Disease, vol. 64 No. 7, pp. 652-657, published Jul. 1980 by American Phytopathological Society.*

(Continued)

*Primary Examiner* — Richard Schnizer
*Assistant Examiner* — Yanzhi Zhang
(74) *Attorney, Agent, or Firm* — Birch, Stewart, Kolasch & Birch, LLP

(57) ABSTRACT

The present invention provides a composition having an excellent controlling activity on plant disease. The composition comprising the compound represented by the formula (1) and one or more inorganic fungicidal compound selected from the group (A) shows an excellent controlling activity on a plant disease. group (A): a group consisting of fludioxonil, pencycuron, ametoctradin, chloroneb, chlorothalonil, oxine-copper, cyflufenamid, dichlofluanid, dicloran, diethofencarb, dinocap, dithianon, edifenphos, fenaminosulf, fentin, fluazinam, fluoroimide, flusulfamide, flutianil, fosetyl-Al, hydrargaphen, iprobenfos, metrafenon, milneb, penflufen, phosdiphen, phthalide, prothiocarb, pyrazophos, sedaxane, silthiofam, spiroxamine, tebufloquin, and tolyfluanid.

(1)

$CH_3O$ / $NHCH_3$ / O / O / $CH_3$ / $H_3C$

7 Claims, No Drawings

(56) References Cited

OTHER PUBLICATIONS

International Preliminary Report on Patentability for International Patent Application No. PCT/JP2011/055438, dated Sep. 4, 2012.
International Search Report for PCT/JP2011/055438 dated Nov. 18, 2011.
Written Opinion of the International Searching Authority for PCT/JP2011/055438 dated Nov. 18, 2011.
The Office Action (including English translation), dated Aug. 22, 2013, issued in the corresponding Chinese Patent Application No. 201180012297.8.
The Office Action (including an English translation), dated Jun. 16, 2014, issued in the corresponding Mexican Patent Application No. MX/a/2012/009665.
The Pesticide Manual, 15th Edition, Published by British Crop Protection Council (BCPC), Nov. 2009, ISBN 1901396188 (30 pages).

* cited by examiner

PLANT DISEASE CONTROLLING COMPOSITION AND METHOD FOR CONTROLLING PLANT DISEASE

TECHNICAL FIELD

The present invention relates to a plant disease controlling composition and a method for controlling a plant disease.

BACKGROUND ART

Hitherto, there has been provided compounds as an active ingredient for a composition for controlling plant disease (see e.g., WO 05/087773 pamphlet; WO 03/010149 pamphlet; WO 03/074491 pamphlet and WO 01/092231 pamphlet; and The Pesticide Manual—15th edition (BCPC published) ISBN 1901396188; and SHIBUYA INDEX 13th Edition (SHIBUYA INDEX RESEARCH GROUP published)).

Also there has been provided a compound of the formula (1):

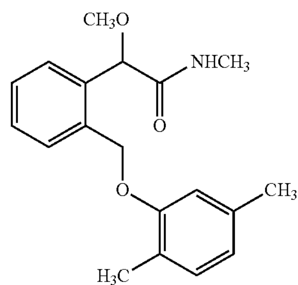

(see e.g., WO 95/27693 pamphlet and WO 02/10101 pamphlet).

DISCLOSURE OF INVENTION

An object of the present invention is to provide a composition having an excellent control effect on a plant disease.

The present inventors have intensively studied to find out a composition having an excellent control effect on a plant disease. As a result, they have found that a composition comprising a compound represented by the formula (1) and one or more inorganic fungicidal compound selected from the following group (A) shows a synergistic activity, and thus has an excellent control effect on a plant disease, and therefore the present invention has been completed.

The present invention provides:

[1] A plant disease controlling composition comprising a compound represented by the formula (1):

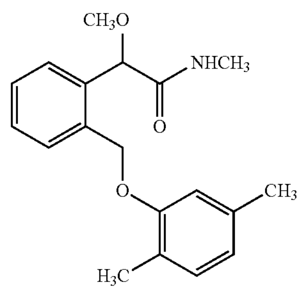

and one or more inorganic fungicidal compound selected from the following group (A):

group (A): a group consisting of fludioxonil, pencycuron, ametoctradin, chloroneb, chlorothalonil, oxine-copper, cyflufenamid, dichlofluanid, dicloran, diethofencarb, dinocap, dithianon, edifenphos, fenaminosulf, fentin, fluazinam, fluoroimide, flusulfamide, flutianil, fosetyl-Al, hydrargaphen, iprobenfos, metrafenon, milneb, penflufen, phosdiphen, phthalide, prothiocarb, pyrazophos, sedaxane, silthiofam, spiroxamine, tebufloquin, and tolyfluanid.

[2] The plant disease controlling composition according to the above [1], wherein a weight ratio of the compound represented by the formula (1) to the inorganic fungicidal compound is that of the compound represented by the formula (1)/the inorganic fungicidal compound=0.0125/1 to 500/1.

[3] The plant disease controlling composition according to the above [1] or [2], wherein the compound represented by the formula (1) is that represented by the formula (1) having R— absolute configuration.

[4] A method for controlling a plant disease which comprises applying each effective amount of the compound of the formula (1):

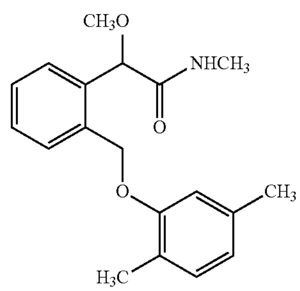

and one or more inorganic fungicidal compound selected from the following group (A) to a plant or a soil for cultivating the plant, group (A): a group consisting of fludioxonil, pencycuron, ametoctradin, chloroneb, chlorothalonil, oxine-copper, cyflufenamid, dichlofluanid, dicloran, diethofencarb, dinocap, dithianon, edifenphos, fenaminosulf, fentin, fluazinam, fluoroimide, flusulfamide, flutianil, fosetyl-Al, hydrargaphen, iprobenfos, metrafenon, milneb, penflufen, phosdiphen, phthalide, prothiocarb, pyrazophos, sedaxane, silthiofam, spiroxamine, tebufloquin, and tolyfluanid.

[5] The method for controlling a plant disease according to the above [4], wherein the plant or the soil for cultivating the plant is a seed.

[6] The method for controlling a plant disease according to the above [4] or [5], wherein a weight ratio of the compound represented by the formula (1) to the inorganic fungicidal compound is that of the compound represented by the formula (1)/the inorganic fungicidal compound=0.0125/1 to 500/1.

[7] The method for controlling a plant disease according to any one of the above [4] to [6], wherein the compound represented by the formula (1) is that represented by the formula (1) having R— absolute configuration.

[8] A use of a combination of the compound represented by the formula (1):

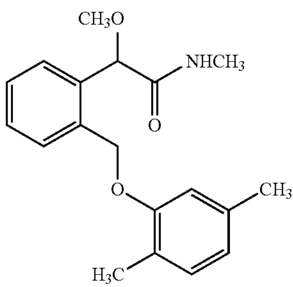

and one or more inorganic fungicidal compound selected from the following group (A) for controlling a plant disease, group (A): a group consisting of fludioxonil, pencycuron, ametoctradin, chloroneb, chlorothalonil, oxine-copper, cyflufenamid, dichlofluanid, dicloran, diethofencarb, dinocap, dithianon, edifenphos, fenaminosulf, fentin, fluazinam, fluoroimide, flusulfamide, flutianil, fosetyl-Al, hydrargaphen, iprobenfos, metrafenon, milneb, penflufen, phosdiphen, phthalide, prothiocarb, pyrazophos, sedaxane, silthiofam, spiroxamine, tebufloquin, and tolyfluanid.

The present invention enables to control a plant disease.

BEST MODE FOR CARRYING OUT THE INVENTION

A plant disease controlling composition of the present invention (hereinafter, referred to as a composition of the present invention) comprises a compound represented by the formula (1):

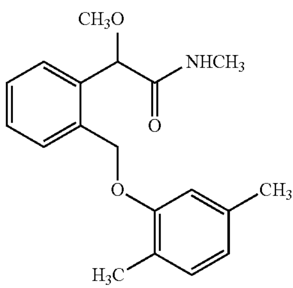

(hereinafter, referred to as an amide compound of the present invention) and one or more inorganic compound selected from the following group (A) (hereinafter, referred to as a inorganic compound of the present invention), group (A): a group consisting of fludioxonil, pencycuron, ametoctradin, chloroneb, chlorothalonil, oxine-copper, cyflufenamid, dichlofluanid, dicloran, diethofencarb, dinocap, dithianon, edifenphos, fenaminosulf, fentin, fluazinam, fluoroimide, flusulfamide, flutianil, fosetyl-Al, hydrargaphen, iprobenfos, metrafenon, milneb, penflufen, phosdiphen, phthalide, prothiocarb, pyrazophos, sedaxane, silthiofam, spiroxamine, tebufloquin, and tolyfluanid.

The present amide compounds are those described in for example, WO 95/27693 pamphlet and WO 02/10101 pamphlet, and thus can be prepared according to the method described therein.

The present amide compound has one asymmetric carbon. Herein, a compound represented by the formula (1) wherein an enantiomer having R— absolute configuration is enriched is referred to as the amide compound having R— absolute configuration.

The present amide compound encompasses the following compounds:

a compound represented by the formula (1) which is contained an enantiomer having R— absolute configuration in 70% and more;

a compound represented by the formula (1) which is contained an enantiomer having R— absolute configuration in 90% and more;

a compound represented by the formula (1) which is contained an enantiomer having R— absolute configuration in 95% and more.

Fludioxonil, pencycuron, ametoctradin, chloroneb, chlorothalonil, oxine-copper, cyflufenamid, dichlofluanid, dicloran, diethofencarb, dinocap, dithianon, edifenphos, fenaminosulf, fentin, fluazinam, fluoroimide, flusulfamide, flutianil, fosetyl-Al, hydrargaphen, iprobenfos, metrafenon, milneb, penflufen, phosdiphen, phthalide, prothiocarb, pyrazophos, sedaxane, silthiofam, spiroxamine, tebufloquin, and tolyfluanid that used in the present invention are all known compounds. Fludioxonil, pencycuron, chloroneb, chlorothalonil, oxine-copper, cyflufenamid, dichlofluanid, dicloran, diethofencarb, dinocap, dithianon, edifenphos, fenaminosulf, fentin, fluazinam, fluoroimide, flusulfamide, flutianil, fosetyl-Al, iprobenfos, metrafenon, milneb, phosdiphen, phthalide, prothiocarb, pyrazophos, silthiofam, spiroxamine, and tolyfluanid are described in for example, "The PESTICIDE MANUAL—15th EDITION (BCPC published) ISBN 1901396188", pages 520, 871, 150, 197, 852, 261, 328, 345, 351, 388, 402, 417, 1231, 491, 513, 537, 556, 558, 575, 664, 786, 1246, 1251, 904, 1254, 976, 1030, 1049 and 1137 respectively. Ametoctradin, penflufen, sedaxane, and tebufloquin are described in WO 05/087773, WO 03/010149, WO 03/074491, and WO 01/092231 respectively. Hydrargaphen is a compound of CAS No. 14235-86-0. These compounds are either commercially available, or can be prepared by a known method.

The weight ratio of the present amide compound to the present inorganic compound in the composition of the present invention is usually that of the present compound/the present inorganic compound=0.0125/1 to 500/1, preferably 0.025/1 to 100/1, and more preferably 0.1/1 to 10/1.

Although the composition of the present invention may be a mixture as itself of the present amide compound and the present inorganic compound, the composition of the present invention is usually prepared by mixing the present amide compound, the present inorganic compound and an inert carrier, and if necessary, adding a surfactant or other pharmaceutical additives, and then formulating into the form of oil solution, emulsifiable concentrate, flowable formulation, wettable powder, granulated wettable powder, dust formulation, granules and so on. Such formulations can be used by itself or with an addition of other inert components as an agent for controlling a plant disease.

Usually, the composition of the present invention can contain 0.1 to 99% by weight, preferably 0.2 to 90% by weight, and more preferably 1 to 80% by weight of the present amide compound and the present inorganic compound in total.

Examples of a solid carrier used on the formulation include finely-divided power or particles of clay consisting of minerals (e.g., kaolin clay, attapulgite clay, bentonite, montmorillonite, acid clay, pyrophyllite, talc, diatomaceous earth, or calcite), natural organic substances (e.g., corncob powder, or walnut shell powder), synthetic organic substances (e.g., urea), salts (e.g., calcium carbonate, or ammonium sulfate), synthetic inorganic substances (e.g., synthetic hydrous silicon oxide) and so on. Examples of a liquid carrier include aromatic hydrocarbons (e.g., xylene, alkyl benzene, or methylnaphtalene), alcohols (e.g., 2-propanol, ethylene glycol, propylene glycol, or ethylene glycol monoethyl ether), ketones (e.g., acetone, cyclohexanone, or isophorone), vegetable oils (e.g., soybean oil, or cotton oils), petroleum-derived aliphatic hydrocarbons, esters, dimethylsulfoxide, acetonitrile and water.

Examples of the surfactant include anionic surfactant (e.g., alkyl sulfate salts, alkylaryl sulfate salts, dialkyl sulfosuccinate salts, polyoxyethylene alkylaryl ether phosphates, lignin sulfonate, or naphthalenesulfonate formaldehyde polycondensation), nonionic surfactant (e.g., polyoxyethylene alkylaryl ether, polyoxyethylene alkyl polyoxypropylene block copolymer, or sorbitan fatty acid ester) and cationic surfactant (e.g., alkyltrimethyl ammonium salts).

Examples of the other pharmaceutical additives include water-soluble polymer (e.g., polyvinyl alcohol, or polyvinyl pyrrolidone), polysaccharides (e.g. arabic gum, alginic acid and salts thereof, CMC (carboxymethyl-cellulose), or xanthan gum), inorganic substances (e.g, aluminum magnesium silicate, or alumina-sol), antiseptic agent, coloring agent, and PAP (isopropyl acid phosphate), and stabilizing agent (e.g., BHT).

The composition of the present invention can also be prepared by separately formulating the present amide compound and the present inorganic compound into different formulations by the above procedures, if necessary, further diluting each of them with water, thereafter, mixing the separately prepared different formulations or the dilute solutions.

The composition of the present invention may further contain one or more other fungicide and/or insecticide.

The composition of the present invention is used to control a plant disease by applying it to a plant or a soil for cultivating the plant.

The plant disease which can be controlled by the present invention is exemplified below:

Rice diseases: blast (*Magnaporthe oryzae*) *helminthosporium* leaf spot (*Cochliobolus miyabeanus*), sheath blight (*Rhizoctonia solani*) and bakanae disease (*Gibberella fujikuroi*);

Diseases of barley, wheat, oats and rye: powdery mildew (*Erysiphe graminis*), *Fusarium* head blight (*Fusarium graminearum, F. avenaceum, F. culmorum, F. asiatricum, Microdochium nivale*), rust (*Puccinia striiformis, P. graminis, P. recondite, P. hordei*), snow blight (*Typhula* sp., *Micronectriella nivalis*) loose smut (*Ustilago tritici, U. nuda*), bunt (*Tilletia caries*), eyespot (*Pseudocercosporella herpotrichoides*) scald (*Rhynchosporium secalis*), leaf blotch (*Septoria tritici*), glume blotch (*Leptosphaeria nodorum*) and net blotch (*Pyrenophora teres Drechsler*);

Citrus diseases: melanose (*Diaporthe citri*), scab (*Elsinoe fawcetti*) and *Penicillium* rot (*Penicillium digitatum, P. italicum*);

Apple diseases: blossom blight (*Monilinia mali*), canker (*Valsa ceratosperma*), powdery mildew (*Podosphaera leucotricha*), *Alternaria* leaf spot (*Alternaria alternata* apple pathotype), scab (*Venturia inaequalis*), bitter rot (*Colletotrichum acutatum*) and late blight (*Phytophtora cactorum*);

Pear diseases: scab (*Venturia nashicola, V. pirina*), black spot (*Alternaria alternate* Japanese pear pathotype), rust (*Gymnosporangium haraeanum*) and late blight (*Phytophtora cactorum*);

Peach diseases: brown rot (*Monilinia fructicola*), scab (*Cladosporium carpophilum*) and *Phomopsis* rot (*Phomopsis* sp.);

Grapes diseases: anthracnose (*Elsinoe ampelina*), ripe rot (*Glomerella cingulata*), powdery mildew (*Uncinula necator*), rust (*Phakopsora ampelopsidis*), black rot (*Guignardia bidwellii*), downy mildew (*Plasmopara viticola*) and Gray mold (*Botrytis cinerea*);

Diseases of Japanese persimmon: anthracnose (*Gloeosporiura kaki*) and leaf spot (*Cercospora kaki, Mycosphaerella nawae*);

Diseases of gourd family: anthracnose (*Colletotrichum lagenarium*), powdery mildew (*Sphaerotheca fuliginea*), gummy stem blight (*Mycosphaerella melonis*), *Fusarium* wilt (*Fusarium oxysporum*), downy mildew (*Pseudoperonospora cubensis*) *Phytophthora* rot (*Phytophthora* sp.) and damping-off (*Pythium* sp.);

Tomato diseases: early blight (*Alternaria solani*), leaf mold (*Cladosporium fulvum*) and late blight (*Phytophthora infestans*);

Egg plant disease: brown spot (*Phomopsis vexans*) and powdery mildew (*Erysiphe cichoracearum*);

Diseases of Cruciferous Vegetables: *Alternaria* leaf spot (*Alternaria japonica*), white spot (*Cercosporella brassicae*), clubroot (*Plasmodiophora brassicae*), and downy mildew (*Peronospora parasitica*);

Rapeseed diseases: *Sclerotinia* rot (*Sclerotinia sclerotiorum*), black spot (*Alternaria brassicae*), powdery mildew (*Erysiphe cichoracearum*), blackleg (*Leptosphaeria maculans*);

Welsh onion diseases: rust (*Puccinia allii*);

Soybean diseases: purple seed stain (*Cercospora kikuchii*), *Sphaceloma* scad (*Elsinoe glycines*), pod and stem blight (*Diaporthe phaseolorum* var. *sojae*), rust (*Phakopsora pachyrhizi*) and *phytophthora* stem rot (*Phytophthora sojae*);

Adzuki-bean diseases: Gray mold (*Botrytis cinerea*), *Sclerotinia* rot (*Sclerotinia sclerotiorum*);

Kidney bean diseases: Gray mold (*Botrytis cinerea*), *Sclerotinia* rot (*Sclerotinia sclero tiorum*), anthracnose (*Colletotrichum lindemthianum*);

Peanut diseases: leaf spot (*Cercospora personata*), brown leaf spot (*Cercospora arachidicola*) and southern blight (*Sclerotium rolfsii*);

Garden pea diseases: powdery mildew (*Erysiphe pisi*);

Potato diseases: early blight (*Alternaria solani*) and late blight (*Phytophthora infestans*);

Strawberry diseases: powdery mildew (*Sphaerotheca humuli*);

Tea diseases: net blister blight (*Exobasidium reticulatum*) white scab (*Elsinoe leucospila*), gray blight (*Pestalotiopsis* sp.) and anthracnose (*Colletotrichum theae-sinensis*);

Cotton diseases: *fusarium* wilt (*Fusarium oxysporum*), damping-off (*Rhizoctonia solani*);

Tabacco diseases: brown spot (*Alternaria longipes*), powdery mildew (*Erysiphe cichoracearum*), anthracnose (*Colletotrichum tabacum*) downy mildew (*Peronospora tabacina*) and late blight (*Phytophthora nicotianae*);

Sugar beet diseases: *Cercospora* leaf spot (*Cercospora beticola*), leaf blight (*Thanatephorus cucumeris*), Root rot (*Aphanidermatum cochlioides*);

Rose diseases: black spot (*Diplocarpon rosae*) and powdery mildew (*Sphaerotheca pannosa*);

Chrysanthemum diseases: leaf blight (*Septoria chrysanthemi-indici*) and white rust (*Puccinia horiana*);

Various plants diseases: diseases caused by *Pythium* spp. (*Pythium aphanidermatum, Pythium debarianum, Pythium graminicola, Pythium irregulare, Pythium ultimum*), Gray mold (*Botrytis cinerea*), *Sclerotinia* rot (*Sclerotinia sclerotiorum*), Japanese radish diseases: *Alternaria* leaf spot (*Alternaria brassicicola*);

Turfgrass diseases: dollar spot (*Sclerotinia homeocarpa*), brown patch and large patch (*Rhizoctonia solani*); and Banana diseases: Sigatoka disease (*Mycosphaerella fijiensis, Mycosphaerella musicola, Pseudocercospora musae*).

Examples of the plants to which the composition of the present invention can be applied are as follows:

Crops: corn, rice, wheat, barley, rye, oat, sorghum, cotton, soybean, adzuki-bean, kidney bean, peanut, buckwheat, beet, rapeseed, sunflower, sugar cane, and tobacco, etc.;

Vegetables: solanaceous vegetables (eggplant, tomato, pimento, pepper, and potato, etc.), cucurbitaceous vegetables (cucumber, pumpkin, zucchini, water melon, melon, and squash, etc.), cruciferous vegetables (Japanese radish, white turnip, horseradish, kohlrabi, Chinese cabbage, cabbage, leaf mustard, broccoli, and cauliflower, etc.), asteraceous vegetables (burdock, crown daisy, artichoke, and lettuce, etc.), liliaceous vegetables (green onion, onion, garlic, and asparagus), ammiaceous vegetables (carrot, parsley, celery, and parsnip, etc.) chenopodiaceous vegetables (spinach, and Swiss chard, etc.), lamiaceous vegetables (*Perilla frutescens*, mint, and basil, etc.), strawberry, sweet potato, Dioscorea japonica, and colocasia, etc.;

Flowers;

Foliage plants;

Turfgrass;

Fruits: pomaceous fruits (apple, pear, Japanese pear, Chinese quince, and quince, etc.), stone fleshy fruits (peach, plum, nectarine, *Prunus* mume, cherry fruit, apricot, and prune, etc.), citrus fruits (*Citrus unshiu*, orange, lemon, lime, and grapefruit, etc.), nuts (chestnut, walnuts, hazelnuts, almond, pistachio, cashew nuts, and *macadamia* nuts, etc.), berrys (blueberry, cranberry, blackberry, and raspberry, etc.), grape, kaki fruit, olive, Japanese plum, banana, coffee, date palm, and coconuts, etc.; and Trees other than fruit trees: tea, mulberry, flowering plant, roadside trees (ash, birch, dogwood, Eucalyptus, *Ginkgo biloba*, lilac, maple, *Quercus*, poplar, Judas tree, *Liquidambar formosana*, plane tree, zelkova, Japanese arborvitae, fir wood, hemlock, juniper, *Pinus, Picea*, and *Taxus cuspidate*), etc.

The aforementioned "plants" include plants which resistance has been imparted by genetic recombination.

Exemplary embodiments of the composition of the present invention are as follows:

a composition comprising the present amide compound and fludioxonil wherein a weight ratio thereof is that of the present amide compound/fludioxonil=0.0125/1 to 500/1;

a composition comprising the present amide compound and fludioxonil wherein a weight ratio thereof is that of the present amide compound/fludioxonil=0.05/1 to 20/1;

a composition comprising the present amide compound and fludioxonil wherein a weight ratio thereof is that of the present amide compound/fludioxonil=0.2/1 to 5/1;

a composition comprising the present amide compound and pencycuron wherein a weight ratio thereof is that of the present amide compound/pencycuron=0.0125/1 to 500/1; a composition comprising the present amide compound and pencycuron wherein a weight ratio thereof is that of the present amide compound/pencycuron=0.025/1 to 100/1;

a composition comprising the present amide compound and pencycuron wherein a weight ratio thereof is that of the present amide compound/pencycuron=0.1/1 to 10/1;

a composition comprising the present amide compound and ametoctradin wherein a weight ratio thereof is that of the present amide compound/ametoctradin=0.0125/1 to 500/1;

a composition comprising the present amide compound and ametoctradin wherein a weight ratio thereof is that of the present amide compound/ametoctradin=0.025/1 to 100/1;

a composition comprising the present amide compound and ametoctradin wherein a weight ratio thereof is that of the present amide compound/ametoctradin=0.1/1 to 10/1;

a composition comprising the present amide compound and chloroneb wherein a weight ratio thereof is that of the present amide compound/chloroneb=0.0125/1 to 500/1;

a composition comprising the present amide compound and chloroneb wherein a weight ratio thereof is that of the present amide compound/chloroneb=0.025/1 to 100/1;

a composition comprising the present amide compound and chloroneb wherein a weight ratio thereof is that of the present amide compound/chloroneb=0.1/1 to 10/1;

a composition comprising the present amide compound and chlorothalonil wherein a weight ratio thereof is that of the present amide compound/chlorothalonil=0.0125/1 to 500/1;

a composition comprising the present amide compound and chlorothalonil wherein a weight ratio thereof is that of the present amide compound/chlorothalonil=0.05/1 to 20/1;

a composition comprising the present amide compound and chlorothalonil wherein a weight ratio thereof is that of the present amide compound/chlorothalonil=0.2/1 to 5/1;

a composition comprising the present amide compound and oxine-copper wherein a weight ratio thereof is that of the present amide compound/oxine-copper=0.0125/1 to 500/1;

a composition comprising the present amide compound and oxine-copper wherein a weight ratio thereof is that of the present amide compound/oxine-copper=0.025/1 to 100/1;

a composition comprising the present amide compound and oxine-copper wherein a weight ratio thereof is that of the present amide compound/oxine-copper=0.1/1 to 10/1;

a composition comprising the present amide compound and cyflufenamid wherein a weight ratio thereof is that of the present amide compound/cyflufenamid=0.0125/1 to 500/1;

a composition comprising the present amide compound and cyflufenamid wherein a weight ratio thereof is that of the present amide compound/cyflufenamid=0.025/1 to 100/1;

a composition comprising the present amide compound and cyflufenamid wherein a weight ratio thereof is that of the present amide compound/cyflufenamid=0.1/1 to 10/1;

a composition comprising the present amide compound and dichlofluanid wherein a weight ratio thereof is that of the present amide compound/dichlofluanid=0.0125/1 to 500/1;

a composition comprising the present amide compound and dichlofluanid wherein a weight ratio thereof is that of the present amide compound/dichlofluanid=0.05/1 to 20/1;

a composition comprising the present amide compound and dichlofluanid wherein a weight ratio thereof is that of the present amide compound/dichlofluanid=0.2/1 to 5/1;

a composition comprising the present amide compound and dicloran wherein a weight ratio thereof is that of the present amide compound/dicloran=0.0125/1 to 500/1;

a composition comprising the present amide compound and dicloran wherein a weight ratio thereof is that of the present amide compound/dicloran=0.05/1 to 20/1;

a composition comprising the present amide compound and dicloran wherein a weight ratio thereof is that of the present amide compound/dicloran=0.2/1 to 5/1;

a composition comprising the present amide compound and diethofencarb wherein a weight ratio thereof is that of the present amide compound/diethofencarb=0.0125/1 to 500/1;

a composition comprising the present amide compound and diethofencarb wherein a weight ratio thereof is that of the present amide compound/diethofencarb=0.05/1 to 20/1;

a composition comprising the present amide compound and diethofencarb wherein a weight ratio thereof is that of the present amide compound/diethofencarb=0.2/1 to 5/1;

a composition comprising the present amide compound and dinocap wherein a weight ratio thereof is that of the present amide compound/dinocap=0.0125/1 to 500/1;

a composition comprising the present amide compound and dinocap wherein a weight ratio thereof is that of the present amide compound/dinocap=0.025/1 to 100/1;

a composition comprising the present amide compound and dinocap wherein a weight ratio thereof is that of the present amide compound/dinocap=0.1/1 to 10/1;

a composition comprising the present amide compound and dithianon wherein a weight ratio thereof is that of the present amide compound/dithianon=0.0125/1 to 500/1;

a composition comprising the present amide compound and dithianon wherein a weight ratio thereof is that of the present amide compound/dithianon=0.025/1 to 100/1;

a composition comprising the present amide compound and dithianon wherein a weight ratio thereof is that of the present amide compound/dithianon=0.1/1 to 10/1;

a composition comprising the present amide compound and edifenphos wherein a weight ratio thereof is that of the present amide compound/edifenphos=0.0125/1 to 500/1;

a composition comprising the present amide compound and edifenphos wherein a weight ratio thereof is that of the present amide compound/edifenphos=0.025/1 to 100/1;

a composition comprising the present amide compound and edifenphos wherein a weight ratio thereof is that of the present amide compound/edifenphos=0.1/1 to 10/1;

a composition comprising the present amide compound and fenaminosulf wherein a weight ratio thereof is that of the present amide compound/fenaminosulf=0.0125/1 to 500/1;

a composition comprising the present amide compound and fenaminosulf wherein a weight ratio thereof is that of the present amide compound/fenaminosulf=0.025/1 to 100/1;

a composition comprising the present amide compound and fenaminosulf wherein a weight ratio thereof is that of the present amide compound/fenaminosulf=0.1/1 to 10/1;

a composition comprising the present amide compound and fentin wherein a weight ratio thereof is that of the present amide compound/fentin=0.0125/1 to 500/1;

a composition comprising the present amide compound and fentin wherein a weight ratio thereof is that of the present amide compound/fentin=0.025/1 to 100/1;

a composition comprising the present amide compound and fentin wherein a weight ratio thereof is that of the present amide compound/fentin=0.1/1 to 10/1;

a composition comprising the present amide compound and fluazinam wherein a weight ratio thereof is that of the present amide compound/fluazinam=0.0125/1 to 500/1;

a composition comprising the present amide compound and fluazinam wherein a weight ratio thereof is that of the present amide compound/fluazinam=0.05/1 to 20/1;

a composition comprising the present amide compound and fluazinam wherein a weight ratio thereof is that of the present amide compound/fluazinam=0.2/1 to 5/1;

a composition comprising the present amide compound and fluoroimide wherein a weight ratio thereof is that of the present amide compound/fluoroimide=0.0125/1 to 500/1;

a composition comprising the present amide compound and fluoroimide wherein a weight ratio thereof is that of the present amide compound/fluoroimide=0.025/1 to 100/1;

a composition comprising the present amide compound and fluoroimide wherein a weight ratio thereof is that of the present amide compound/fluoroimide=0.1/1 to 10/1;

a composition comprising the present amide compound and flusulfamide wherein a weight ratio thereof is that of the present amide compound/flusulfamide=0.0125/1 to 500/1;

a composition comprising the present amide compound and flusulfamide wherein a weight ratio thereof is that of the present amide compound/flusulfamide=0.025/1 to 100/1;

a composition comprising the present amide compound and flusulfamide wherein a weight ratio thereof is that of the present amide compound/flusulfamide=0.1/1 to 10/1;

a composition comprising the present amide compound and flutianil wherein a weight ratio thereof is that of the present amide compound/flutianil=0.0125/1 to 500/1;

a composition comprising the present amide compound and flutianil wherein a weight ratio thereof is that of the present amide compound/flutianil=0.025/1 to 100/1;

a composition comprising the present amide compound and flutianil wherein a weight ratio thereof is that of the present amide compound/flutianil=0.1/1 to 10/1;

a composition comprising the present amide compound and fosetyl-Al wherein a weight ratio thereof is that of the present amide compound/fosetyl-Al=0.0125/1 to 500/1;

a composition comprising the present amide compound and fosetyl-Al wherein a weight ratio thereof is that of the present amide compound/fosetyl-Al=0.05/1 to 20/1;

a composition comprising the present amide compound and fosetyl-Al wherein a weight ratio thereof is that of the present amide compound/fosetyl-Al=0.2/1 to 5/1;

a composition comprising the present amide compound and hydrargaphen wherein a weight ratio thereof is that of the present amide compound/hydrargaphen=0.0125/1 to 500/1;

a composition comprising the present amide compound and hydrargaphen wherein a weight ratio thereof is that of the present amide compound/hydrargaphen=0.025/1 to 100/1;

a composition comprising the present amide compound and hydrargaphen wherein a weight ratio thereof is that of the present amide compound/hydrargaphen=0.1/1 to 10/1;

a composition comprising the present amide compound and iprobenfos wherein a weight ratio thereof is that of the present amide compound/iprobenfos=0.0125/1 to 500/1;

a composition comprising the present amide compound and iprobenfos wherein a weight ratio thereof is that of the present amide compound/iprobenfos=0.025/1 to 100/1;

a composition comprising the present amide compound and iprobenfos wherein a weight ratio thereof is that of the present amide compound/iprobenfos=0.1/1 to 10/1;

a composition comprising the present amide compound and metrafenon wherein a weight ratio thereof is that of the present amide compound/metrafenon=0.0125/1 to 500/1;

a composition comprising the present amide compound and metrafenon wherein a weight ratio thereof is that of the present amide compound/metrafenon=0.025/1 to 100/1;

a composition comprising the present amide compound and metrafenon wherein a weight ratio thereof is that of the present amide compound/metrafenon=0.1/1 to 10/1;

a composition comprising the present amide compound and milneb wherein a weight ratio thereof is that of the present amide compound/milneb=0.0125/1 to 500/1;

a composition comprising the present amide compound and milneb wherein a weight ratio thereof is that of the present amide compound/milneb=0.025/1 to 100/1;

a composition comprising the present amide compound and milneb wherein a weight ratio thereof is that of the present amide compound/milneb=0.1/1 to 10/1;

a composition comprising the present amide compound and penflufen wherein a weight ratio thereof is that of the present amide compound/penflufen=0.0125/1 to 500/1;

a composition comprising the present amide compound and penflufen wherein a weight ratio thereof is that of the present amide compound/penflufen=0.05/1 to 20/1;

a composition comprising the present amide compound and penflufen wherein a weight ratio thereof is that of the present amide compound/penflufen=0.2/1 to 5/1;

a composition comprising the present amide compound and phosdiphen wherein a weight ratio thereof is that of the present amide compound/phosdiphen=0.0125/1 to 500/1;

a composition comprising the present amide compound and phosdiphen wherein a weight ratio thereof is that of the present amide compound/phosdiphen=0.05/1 to 20/1;

a composition comprising the present amide compound and phosdiphen wherein a weight ratio thereof is that of the present amide compound/phosdiphen=0.2/1 to 5/1;

a composition comprising the present amide compound and phthalide wherein a weight ratio thereof is that of the present amide compound/phthalide=0.0125/1 to 500/1;

a composition comprising the present amide compound and phthalide wherein a weight ratio thereof is that of the present amide compound/phthalide=0.05/1 to 20/1;

a composition comprising the present amide compound and phthalide wherein a weight ratio thereof is that of the present amide compound/phthalide=0.2/1 to 5/1;

a composition comprising the present amide compound and prothiocarb wherein a weight ratio thereof is that of the present amide compound/prothiocarb=0.0125/1 to 500/1;

a composition comprising the present amide compound and prothiocarb wherein a weight ratio thereof is that of the present amide compound/prothiocarb=0.025/1 to 100/1;

a composition comprising the present amide compound and prothiocarb wherein a weight ratio thereof is that of the present amide compound/prothiocarb=0.1/1 to 10/1;

a composition comprising the present amide compound and pyrazophos wherein a weight ratio thereof is that of the present amide compound/pyrazophos=0.0125/1 to 500/1;

a composition comprising the present amide compound and pyrazophos wherein a weight ratio thereof is that of the present amide compound/pyrazophos=0.025/1 to 100/1;

a composition comprising the present amide compound and pyrazophos wherein a weight ratio thereof is that of the present amide compound/pyrazophos=0.1/1 to 10/1;

a composition comprising the present amide compound and sedaxane wherein a weight ratio thereof is that of the present amide compound/sedaxane=0.0125/1 to 500/1;

a composition comprising the present amide compound and sedaxane wherein a weight ratio thereof is that of the present amide compound/sedaxane=0.025/1 to 100/1;

a composition comprising the present amide compound and sedaxane wherein a weight ratio thereof is that of the present amide compound/sedaxane=0.1/1 to 10/1;

a composition comprising the present amide compound and silthiofam wherein a weight ratio thereof is that of the present amide compound/silthiofam=0.0125/1 to 500/1;

a composition comprising the present amide compound and silthiofam wherein a weight ratio thereof is that of the present amide compound/silthiofam=0.025/1 to 100/1;

a composition comprising the present amide compound and silthiofam wherein a weight ratio thereof is that of the present amide compound/silthiofam=0.1/1 to 10/1;

a composition comprising the present amide compound and spiroxamine wherein a weight ratio thereof is that of the present amide compound/spiroxamine=0.0125/1 to 500/1;

a composition comprising the present amide compound and spiroxamine wherein a weight ratio thereof is that of the present amide compound/spiroxamine=0.05/1 to 20/1;

a composition comprising the present amide compound and spiroxamine wherein a weight ratio thereof is that of the present amide compound/spiroxamine=0.2/1 to 5/1;

a composition comprising the present amide compound and tebufloquin wherein a weight ratio thereof is that of the present amide compound/tebufloquin=0.0125/1 to 500/1;

a composition comprising the present amide compound and tebufloquin wherein a weight ratio thereof is that of the present amide compound/tebufloquin=0.025/1 to 100/1;

a composition comprising the present amide compound and tebufloquin wherein a weight ratio thereof is that of the present amide compound/tebufloquin=0.1/1 to 10/1;

a composition comprising the present amide compound and tolyfluanid wherein a weight ratio thereof is that of the present amide compound/tolyfluanid=0.0125/1 to 500/1;

a composition comprising the present amide compound and tolyfluanid wherein a weight ratio thereof is that of the present amide compound/tolyfluanid=0.025/1 to 100/1; and a composition comprising the present amide compound and tolyfluanid wherein a weight ratio thereof is that of the present amide compound/tolyfluanid=0.1/1 to 10/1.

The method for controlling a plant disease of the present invention (hereinafter, referred to as the method for controlling of the present invention) is carried out by applying each effective amount of the present amide compound and the present inorganic compound to the plants or the soil for cultivating the plant.

Such the plants may be, for example, foliages of plant, seeds of plant, or bulbs of plant. The bulbs herein are intended to mean bulb, corm, rootstock, tubera, tuberous root and rhizophore.

In the method for controlling of the present invention, the present amide compound and the present inorganic compound may be applied separately around the same time to the plant or the soil for cultivating the plant, but is usually applied as the composition of the present invention in terms of a convenience on applying.

In the method for controlling of the present invention, examples of the method of applying the present amide compound and the inorganic compound include foliage treatment, soil treatment, root treatment and seed treatment.

Such the foliage treatment includes for example, a method of applying the composition of the present invention to a surface of the plant to be cultivated by a foliage application or a stem application.

Such the root treatment includes for example, a method of soaking a whole or a root of the plant into a medicinal solution comprising the present amide compound and the present inorganic compound, and a method of attaching a solid formulation comprising the present amide compound, the present inorganic compound and the solid carrier to a root of the plant.

Such the soil treatment includes for example, soil broadcast, soil incorporation, and irrigation of the medicinal solution to a soil.

Such the seed treatment includes for example, an applying of the composition of the present invention to a seed or a bulb of the plant to be prevented from the plant disease, specifically, for example, a spray treatment by spraying a suspension of the composition of the present invention in a mist form to a surface of a seed or a surface of a bulb, a smear treatment by smearing the wettable powder, the emulsifiable concentrate or the flowable formulation of the composition of the present invention with added by small amounts of water or as itself to a seed or a bulb, an immerse treatment of a seed into a solution of the composition of the present invention for a given time, a film-coating treatment, and a pellet-coating treatment.

Each dose of the present amide compound and the present inorganic compound in the method for controlling of the present invention may be varied depending on a kind of plant to be treated, a kind or a frequency of an occurrence of a plant disease as a control subject, a dosage form, a treatment period, a treatment method, a treatment site, a climate condition, etc. In case of an application to a foliage of the plant or a soil for cultivating the plant, a total amount of the present amide compound and the inorganic compound is usually 1 to 500 g, preferably 2 to 200 g, and more preferably 10 to 100 g, per 1000 $m^2$. Each dose of the present amide compound and the present inorganic compound in the treatment for seed is usually 0.001 to 10 g, and preferably 0.01 to 1 g, per 1 kg of seeds.

The emulsifiable concentrate, the wettable powder or the flowable formulation, etc., is usually applied by diluting them with water, and then spreading them. In this case, usually, each concentration of the present amide compound and the present inorganic compound contain 0.0005 to 2% by weight, and preferably 0.005 to 1% by weight of the present amide compound and the present inorganic compound in total. The dust formulation or the granular formulation, etc, is usually applied as itself without diluting them.

EXAMPLES

Next, the present invention is described in more detail below by the following examples including formulation examples and a test example, but the present invention should not be construed to be limited thereto.

The formulation examples are given below. It is to be noted that in the formulation examples, the term "part" indicates "part by weight".

Formulation 1

5 parts of the present amide compound, 5 parts of fludioxonil, 35 parts of a mixture of white carbon and polyoxyethylene alkylether sulfate ammonium salts (weight ratio 1:1), and 55 parts of water were mixed and the resulting solution was then subjected to fine grinding according to a wet grinding method, so as to obtain a flowable formulation. The same above operations were carried out with pencycuron, ametoctradin, chloroneb, chlorothalonil, oxine-copper, cyflufenamid, dichlofluanid, dicloran, diethofencarb, dinocap, dithianon, edifenphos, fenaminosulf, fentin, fluazinam, fluoroimide, flusulfamide, flutianil, fosetyl-Al, hydrargaphen, iprobenfos, metrafenon, milneb, penflufen, phosdiphen, phthalide, prothiocarb, pyrazophos, sedaxane, silthiofam, spiroxamine, tebufloquin, or tolyfluanid instead of fludioxonil, so as to obtain various types of flowable formulations.

Formulation 2

10 parts of the present amide compound, 5 parts of fludioxonil and 1.5 parts of sorbitan trioleate were mixed into 28 parts of an aqueous solution that contained 2 parts of polyvinyl alcohol, and the mixed solution was then subjected to fine grinding according to a wet grinding method. Thereafter, 45.50 parts of an aqueous solution that contained 0.05 parts of xanthan gum and 0.1 part of aluminum magnesium silicate was added to the resultant, and 10 parts of propylene glycol was further added thereto. The obtained mixture was blended by stirring, so as to obtain the flowable formulation. The same above operations were carried out with pencycuron, ametoctradin, chloroneb, chlorothalonil, oxine-copper, cyflufenamid, dichlofluanid, dicloran, diethofencarb, dinocap, dithianon, edifenphos, fenaminosulf, fentin, fluazinam, fluoroimide, flusulfamide, flutianil, fosetyl-Al, hydrargaphen, iprobenfos, metrafenon, milneb, penflufen, phosdiphen, phthalide, prothiocarb, pyrazophos, sedaxane, silthiofam, spiroxamine, tebufloquin, or tolyfluanid instead of fludioxonil, so as to obtain various types of flowable formulations.

Formulation 3

10 parts of the present amide compound, 40 parts of fludioxonil, 3 parts of calcium lignosulfonate, 2 parts of sodium lauryl sulfate, and 45 parts of synthetic hydrous silicon oxide were fully crushed and mixed, so as to obtain wettable powders. The same above operations were carried out with pencycuron, ametoctradin, chloroneb, chlorothalonil, oxine-copper, cyflufenamid, dichlofluanid, dicloran, diethofencarb, dinocap, dithianon, edifenphos, fenaminosulf, fentin, fluazinam, fluoroimide, flusulfamide, flutianil, fosetyl-Al, hydrargaphen, iprobenfos, metrafenon, milneb, penflufen, phosdiphen, phthalide, prothiocarb, pyrazophos, sedaxane, silthiofam, spiroxamine, tebufloquin, or tolyfluanid instead of fludioxonil, so as to obtain various types of wettable powders.

The test examples are given below.

Test Example 1

To a SUS beaker are added 30 parts of the present compound (racemate), 5 parts of Soprophor FLK (polyoxyethylene tristyrylphenyl ether phosphate, produced by Rhodia Nicca Ltd.), 65 parts of ion-exchange water and 150 parts of glass beads (1.0 mm diameter). The mixture is subjected to grinding at a velocity of 1000 rpm with cooling to 10° C., and thereafter the glass beads are separated, so as to obtain a flowable formulation comprising the present compound (racemate).

True leaf of cucumber is punched out with cork borer to 13 mm in diameter to prepare a leaf disk. In 24 well microwell plate that is dispensed with 1 ml 0.8% water agar, the leaf disk is placed such that the upper side of the leaf is in an upward direction. Thereto is added 20 micro liter a testing solution prepared by mixing the flowable formulation of the present compound (racemate) prepared by the above procedure and a commercial wettable powder of fludioxonil or chlorothalonil to a predetermined concentration to treat the leaf disk.

After confirming that the testing medical solution is dried, conidium of gray mold fungus (*Botrytis cinerea*) is suspended into potato dextrose broth (DIFCO) in a density of about $10^5$ conidium/mL and is then subjected to a spray inoculation. After leaving to stand the leaf disk in a growth chamber set up at 15° C. for four days, an onset area on the leaf is measured and then calculated an onset area rate (hereinafter, referred to as an onset area rate of treated group).

The same operation is carried out with 20 micro liter water instead of 20 micro liter a testing medicine solution to calculate an onset area rate (hereinafter, referred to an onset area rate of non-treated group).

A preventive value is calculated from the above onset area rate of treated group and the onset area rate of non-treated group by the following equation:

$$\text{Preventive value (\%)}=100\times(A-B)/A$$

wherein

A: an onset area rate of treated group

B: an onset area rate of non-treated group

The results are shown in Table 1.

TABLE 1

| | treatment concentration (ppm) | | |
|---|---|---|---|
| | the present amide compound | fludioxonil | preventive value (%) |
| 1 | 2.5 | 0.5 | 97.5 |
| 2 | 1.0 | 5.0 | 100 |

TABLE 2

| | treatment concentration (ppm) | | |
|---|---|---|---|
| | the present amide compound | chlorothalonil | preventive value (%) |
| 1 | 2.5 | 0.5 | 96 |
| 2 | 1.0 | 5.0 | 100 |

Test Example 2

The same operations as described in Test Example 1 are carried out with cyflufenamid, diethofencarb, dithianon, fluazinam, flusulfamide, fosetyl-Al, metrafenon, penflufen, phthalide, sedaxane, spiroxamine or tebufloquin, instead of fludioxonil or chlorothalonil, so as to calculate respective preventive values.

Also for comparison, the same operations as described in Test Example 1 are carried out with the exception that the testing medicine solution is substituted with a predetermined concentration of each dimethyl sulfoxide solution of the present compound (racemate), cyflufenamid, diethofencarb, dithianon, fluazinam, flusulfamide, fosetyl-Al, metrafenon, penflufen, phthalide, sedaxane, spiroxamine or tebufloquin, so as to calculate respective preventive values.

The results are shown in Tables 3 to 14.

TABLE 3

| | treatment concentration (ppm) | | |
|---|---|---|---|
| | the present amide compound | cyflufenamid | preventive value (%) |
| 1 | 2.5 | 0.5 | 100 |
| 2 | 1.0 | 5.0 | 100 |
| | 2.5 | — | 56 |
| | 1.0 | — | 46 |
| | — | 0.5 | 10 |
| | — | 5.0 | 15 |

TABLE 4

| | treatment concentration (ppm) | | |
|---|---|---|---|
| | the present amide compound | diethofencarb | preventive value (%) |
| 1 | 2.5 | 0.5 | 100 |
| 2 | 1.0 | 5.0 | 100 |
| | 2.5 | — | 56 |
| | 1.0 | — | 46 |
| | — | 0.5 | 0 |
| | — | 5.0 | 0 |

TABLE 5

| | treatment concentration (ppm) | | |
|---|---|---|---|
| | the present amide compound | dithianon | preventive value (%) |
| 1 | 2.5 | 0.5 | 100 |
| 2 | 1.0 | 5.0 | 100 |
| | 2.5 | — | 56 |
| | 1.0 | — | 46 |
| | — | 0.5 | 15 |
| | — | 5.0 | 20 |

TABLE 6

| | treatment concentration (ppm) | | |
|---|---|---|---|
| | the present amide compound | fluazinam | preventive value (%) |
| 1 | 2.5 | 0.5 | 100 |
| 2 | 1.0 | 5.0 | 100 |
| | 2.5 | — | 56 |
| | 1.0 | — | 46 |
| | — | 0.5 | 47 |
| | — | 5.0 | 52 |

TABLE 7

| | treatment concentration (ppm) | | |
|---|---|---|---|
| | the present amide compound | flusulfamide | preventive value (%) |
| 1 | 2.5 | 0.5 | 100 |
| 2 | 1.0 | 5.0 | 100 |
| | 2.5 | — | 56 |
| | 1.0 | — | 46 |
| | — | 0.5 | 15 |
| | — | 5.0 | 20 |

TABLE 8

| | treatment concentration (ppm) | | |
|---|---|---|---|
| | the present amidic compound | fosetyl-Al | preventive value (%) |
| 1 | 2.5 | 0.5 | 100 |
| 2 | 1.0 | 5.0 | 100 |
| | 2.5 | — | 56 |
| | 1.0 | — | 46 |
| | — | 0.5 | 15 |
| | — | 5.0 | 20 |

TABLE 9

| | treatment concentration (ppm) | | |
|---|---|---|---|
| | the present amide compound | metrafenon | preventive value (%) |
| 1 | 2.5 | 0.5 | 100 |
| 2 | 1.0 | 5.0 | 100 |
| | 2.5 | — | 56 |
| | 1.0 | — | 46 |
| | — | 0.5 | 10 |
| | — | 5.0 | 15 |

TABLE 10

| | treatment concentration (ppm) | | |
|---|---|---|---|
| | the present amide compound | penflufen | preventive value (%) |
| 1 | 2.5 | 0.5 | 100 |
| 2 | 1.0 | 5.0 | 100 |
| | 2.5 | — | 56 |
| | 1.0 | — | 46 |
| | — | 0.5 | 10 |
| | — | 5.0 | 15 |

TABLE 11

| | treatment concentration (ppm) | | |
|---|---|---|---|
| | the present amide compound | phthalide | preventive value (%) |
| 1 | 2.5 | 0.5 | 100 |
| 2 | 1.0 | 5.0 | 100 |
| | 2.5 | — | 56 |
| | 1.0 | — | 46 |
| | — | 0.5 | 10 |
| | — | 5.0 | 15 |

TABLE 12

| | treatment concentration (ppm) | | |
|---|---|---|---|
| | the present amide compound | sedaxane | preventive value (%) |
| 1 | 2.5 | 0.5 | 100 |
| 2 | 1.0 | 5.0 | 100 |
| | 2.5 | — | 56 |
| | 1.0 | — | 46 |
| | — | 0.5 | 20 |
| | — | 5.0 | 40 |

TABLE 13

| | treatment concentration (ppm) | | |
|---|---|---|---|
| | the present amide compound | spiroxamine | preventive value (%) |
| 1 | 2.5 | 0.5 | 100 |
| 2 | 1.0 | 5.0 | 100 |
| | 2.5 | — | 56 |
| | 1.0 | — | 46 |
| | — | 0.5 | 10 |
| | — | 5.0 | 15 |

TABLE 14

| | treatment concentration (ppm) | | |
|---|---|---|---|
| | the present amide compound | tebufloquin | preventive value (%) |
| 1 | 2.5 | 0.5 | 100 |
| 2 | 1.0 | 5.0 | 100 |
| | 2.5 | — | 56 |
| | 1.0 | — | 46 |
| | — | 0.5 | 10 |
| | — | 5.0 | 15 |

Next, the Reference Example is given below.

Reference Example

For comparison, the same operations as described in Test Example 1 are carried out with the exception that the testing medicine solution is substituted with a predetermined concentration of each dimethyl sulfoxide solution of fludioxonil or chlorothalonil, so as to calculate a preventive value.

The results are shown in Tables 15 to 16.

TABLE 15

| treatment concentration (ppm) fludioxonil | preventive value (%) |
|---|---|
| 0.5 | 45 |
| 5.0 | 57 |

TABLE 16

| treatment concentration (ppm) chlorothalonil | preventive value (%) |
|---|---|
| 0.5 | 15 |
| 5.0 | 45 |

The invention claimed is:

1. A composition for controlling a fungus disease in a plant comprising a compound of formula (1):

(1)

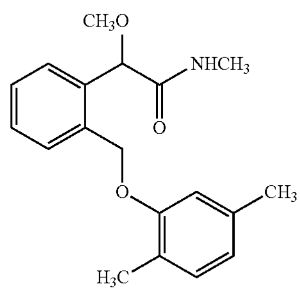

and one or more fungicidal compound selected from the following group (A):

group (A): a group consisting of fludioxonil, chlorothalonil, cyflufenamid, diethofencarb, dithianon, fluazinam, flusulfamide, fosetyl-Al, metrafenon, penflufen, phthalide, sedaxane, spiroxamine, and tebufloquin, wherein a weight ratio of the compound of formula (1) to the one or more fungicidal compound is that of the compound of formula (1)/the fungicidal compound=0.1/1 to 10/1.

2. The composition according to claim 1, wherein the compound of formula (1) possesses an R— absolute configuration.

3. A method for controlling a plant fungus disease which comprises applying an effective amount of each of a compound of formula (1):

(1)

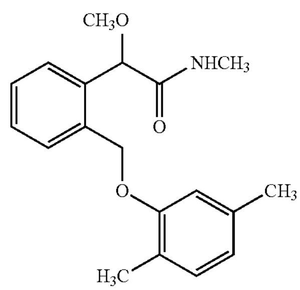

and one or more fungicidal compound selected from the following group (A) to a plant or a soil for cultivating the plant, group (A): a group consisting of fludioxonil, chlorothalonil, cyflufenamid, diethofencarb, dithianon, fluazinam, flusulfamide, fosetyl-Al, metrafenon, penflufen, phthalide, sedaxane, spiroxamine, and tebufloquin, wherein a weight ratio of the compound of formula (1) to the one or more fungicidal compound is that of the compound of formula (1)/the fungicidal compound=0.1/1 to 10/1.

4. The method according to claim 3, wherein the plant or the soil for cultivating the plant is a seed or a soil for cultivating a seed, respectively.

5. The method according to claim 3, wherein the compound of formula (1) possesses an R— absolute configuration.

6. The composition according to claim 1, wherein the one or more fungicidal compound is selected from the following group (A):

group (A): a group consisting of chlorothalonil, cyflufenamid, diethofencarb, dithianon, fluazinam, flusulfamide, fosetyl-Al, metrafenon, penflufen, phthalide, sedaxane, spiroxamine, and tebufloquin.

7. The method according to claim 3, wherein the one or more fungicidal compound is selected from the following group (A):

group (A): a group consisting of chlorothalonil, cyflufenamid, diethofencarb, dithianon, fluazinam, flusulfamide, fosetyl-Al, metrafenon, penflufen, phthalide, sedaxane, spiroxamine, and tebufloquin.

* * * * *